United States Patent [19]

Marianik et al.

[11] Patent Number: 5,305,083
[45] Date of Patent: Apr. 19, 1994

[54] RANDOM ACCESS MONOCHROMATOR

[75] Inventors: Charles G. J. Marianik, Lawrenceville, N.J.; Carlos Zarate; Gilbert M. Levy, both of Ontario, Canada

[73] Assignee: ML Technology Ventures, L.P., Menlo Park, Calif.

[21] Appl. No.: 598,560

[22] Filed: Oct. 16, 1990

[51] Int. Cl.$^5$ .............................. G01J 3/14; G01J 3/18
[52] U.S. Cl. ............................ 356/332; 356/310; 356/328; 356/330; 356/334
[58] Field of Search ............... 356/310, 330, 331, 333, 356/334, 332, 326, 328

[56] References Cited

U.S. PATENT DOCUMENTS 2,823,577  2/1958  Machler .
4,193,691  3/1980  Fjarlie .................. 356/330
4,615,619  10/1986 Fateley ................. 356/310
4,790,654  12/1988 Clarke .................. 356/330
4,799,795  1/1989  Fateley ................. 356/310
4,856,897  8/1989  Fateley et al. .......... 356/310

Primary Examiner—F. L. Evans
Attorney, Agent, or Firm—Lyon & Lyon

[57] ABSTRACT

A random access monochromator is disclosed. This device has no mechanical parts and eliminates the need to scan sequentially the wavelengths of light contained in a light spectrum to select a desired wavelength or wavelengths from the spectrum. The device has high speed switching means, permits one to select multiple wavelengths and bandwidths at the same time, and has the ability to correct for non-linearity in prisms caused by their nonlinear or second order dispersion of light.

14 Claims, 2 Drawing Sheets

RANDOM ACCESS MONOCHROMATOR

FIELD OF THE INVENTION

This invention relates to a novel monochromator. More particularly, the invention relates to a high speed random access monochromator having no mechanically moving parts.

BACKGROUND OF THE INVENTION

A monochromator is a device that splits a broad band of light into individual bands of various wavelengths and individually displays a band or bands of a desired wavelength or wavelengths. A diffraction or transmission grating is customarily used to split the original light band. A grating is similar in function to a modern-day prism. In the past, prisms were used in monochromators to perform the function now performed by gratings.

In present-day monochromators, the grating splits light when the grating is mechanically rotated by a motor, or by hand, past a slit. Thus, the split wavelengths are scanned in the order in which they are found in a light spectrum. Grating type monochromators were developed to solve problems associated with the nonlinear or second order dispersion of light commonly exhibited by prisms.

This invention enables one to vary bandwidths of light. This, in turn, will correct for the aforementioned deficiency in prisms, and thus permits prisms to be used again as dispersive elements in the novel random access monochromators described herein.

DISCUSSION OF PRIOR ART

U.S. Pat. No. 2,823,577 to Machler describes a multiple slit spectrograph having an exit slit photosphere assembly with a plurality of mechanically operated shutters which can be opened in a desired sequence. Only a small number of wavelengths can be utilized in such a device. The wavelengths must be preselected and, once this has been done, the wavelengths selected cannot be changed without repositioning the shutters. Further, mechanical shutters make the process of selecting even one or a few wavelengths slow.

U.S. Pat. No. 4,193,691 to Fjarlie shows a liquid crystal cell slit assembly in a spectrometer. Selective actuation of the cell is carried out to form a split pattern appropriate to the spectral lines of interest in the spectrum of the substance being analyzed. A power supply and a switching mechanism such as rotary or push button manual switches are used to select the electrodes that will receive drive voltages. Preprogrammed switching can also be carried out. Since the medium is not in the form of discreet compartments, only a relatively small number of slits can be used. This, however, precludes the ability to select a large number of wavelengths of choice. And since the actual switching medium is altered to pass or block the light, it is not fully transparent. This causes other properties of the light to be changed. Furthermore, certain wavelengths of light, such as ultraviolet light of wavelengths below 350 nm, are blocked, further limiting the wavelength range.

U.S. Pat. Nos. 4,615,619 and 4,779,795 to Fateley depict a device similar to that shown in Fjarlie U.S. Pat. No. 4,193,691. Selection is done in this case by a mask formed from a dichromatic crystalline or polycrystalline material that can be selectively altered between a relatively transmissive condition and a substantially opaque and relatively reflective condition. Because wavelength selection is done with an active component, the device of the Fateley patents has the same disadvantages as the Fjarlie device.

GENERAL DISCUSSION OF THE INVENTION

People have searched for some time for a way of quickly producing light of desired wavelengths, on command, with no mechanical motion. As an example, one may wish to select first a desired wavelength of 380 nm, then a wavelength of 700 nm, then a wavelength of 320 nm, and lastly a wavelength of 500 nm. To select this sequence of wavelengths using present-day monochromators, one would have to scan the wavelengths in sequential manner, forward, then backward, then forward again, a time consuming procedure which can cause loss of data and limit the usefulness of the device in numerous applications.

This invention is directed to a random access monochromator which, instead of requiring that a plurality of wavelengths be scanned sequentially, permits one to go directly to a desired wavelength or wavelengths. Saved time and the elimination of moving mechanical parts are distinct advantages of this novel instrument. In addition, the ability of the instrument to operate at faster speeds to randomly access a light spectrum opens up a whole new range of applications for the instrument.

The random access monochromator of this invention also allows one to produce a multiplicity of wavelengths at the same time. As many wavelengths as desired can be produced, which again leads to new applications for this instrument.

The novel random access monochromator of this invention is also unique in that one can select at will a variable wavelength bandwidth. This greatly enhances the throughput of light, and permits the instrument, as indicated above, to be used to correct the linearity problems associated with prisms.

The random access capability of this novel monochromator, while enhancing and broadening the applications for which the instrument can be used, does not adversely affect its other desirable features, such as: wavelength range, beam polarization characteristics, throughput, resolution and low scattered light.

BRIEF DESCRIPTION OF THE DRAWINGS

FIG. I is a schematic representation of a random access monochromator of this invention.

FIG. II is a schematic representation of a micro shutter device for use in a random access monochromator of this invention.

Figure 1:
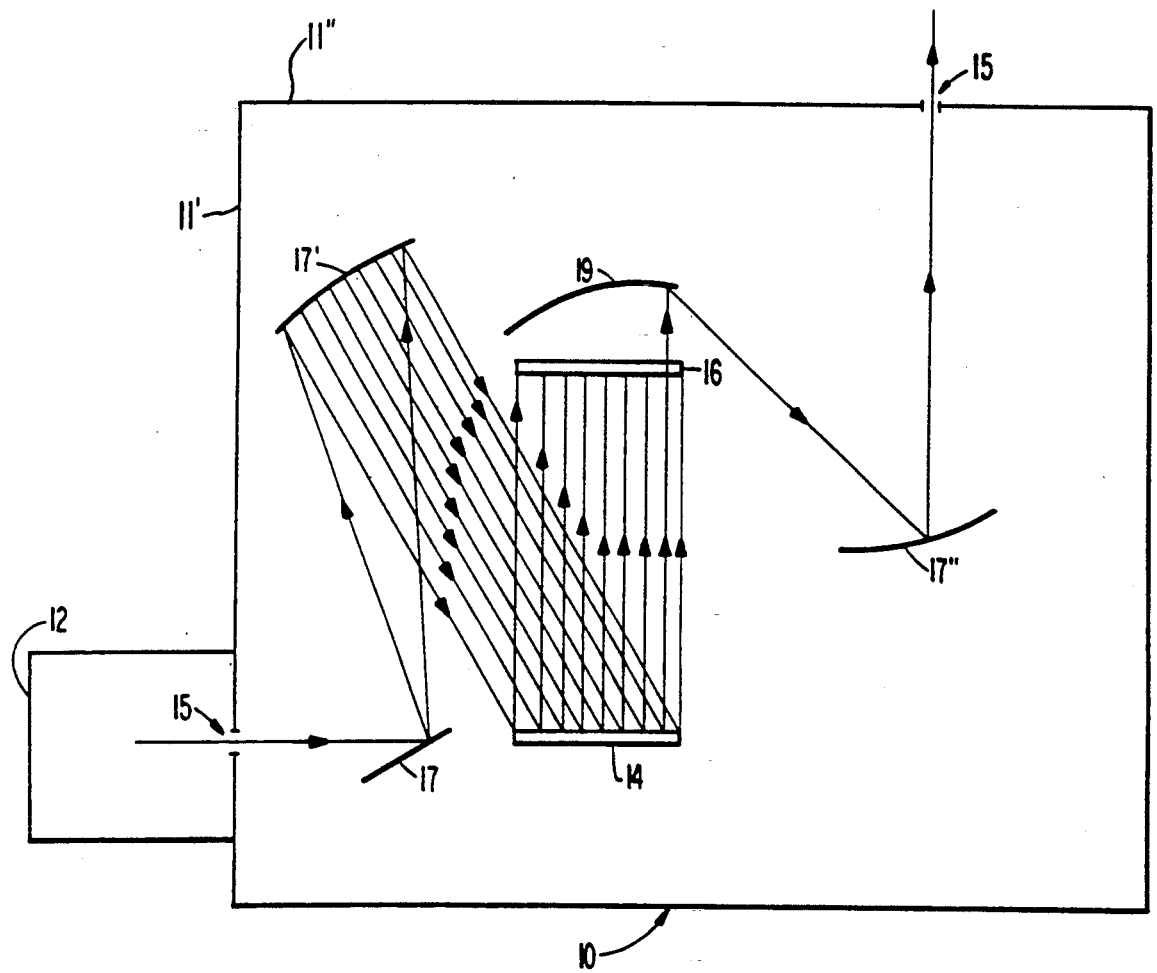
Figure 2:
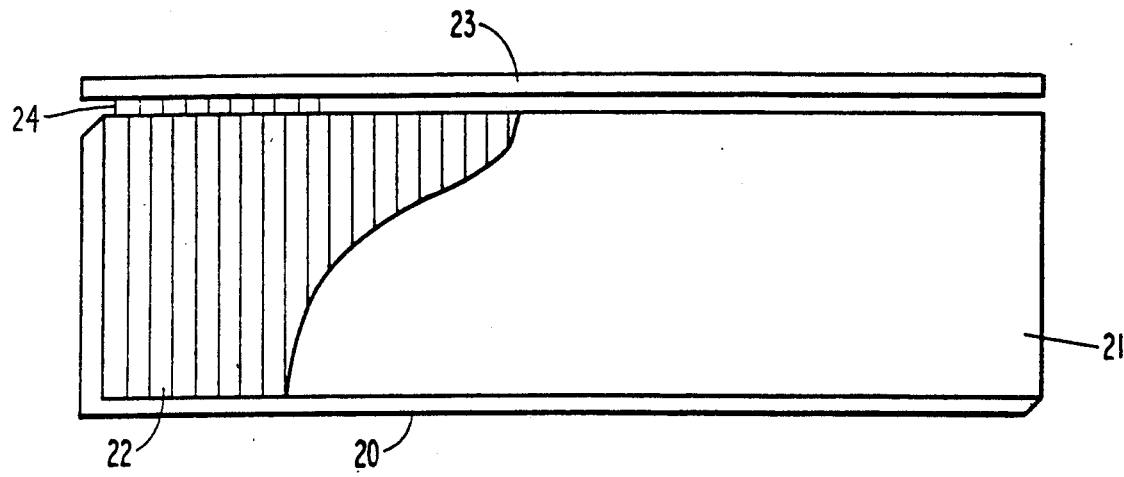
Figure 3:
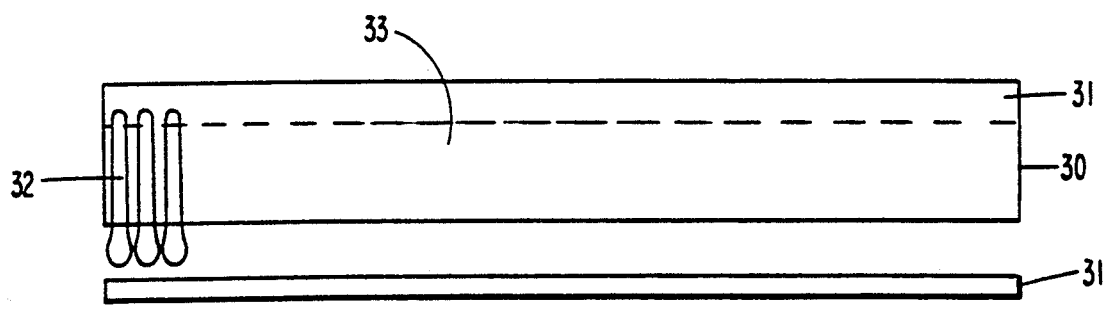

FIG. III is a schematic representation of a micro mercury switch for use in a random access monochromator of this invention.

DETAILED DESCRIPTION OF THE INVENTION

A random access monochromator of this invention, designated generally as 10 in FIG. I including walls 11' and 11", receives light from a light source 12 through a slit 15 in wall 11'. The light source 12 can be any type of light source, including light from a sample, e.g., a fluorescent, luminescent or bioluminescent sample, generating light of any configuration, not necessarily collimated. Non-conventional light sources such as lasers can also be used. The light from the light source 12 is transferred to a grating or gratings 14 by means of reflective mirrors which include, for example, an angularly disposed planar deflecting mirror 17, a concave collecting mirror 17', a concave collecting mirror 19, which can be equivalent in focus to the concave collecting mirror 17', and a deflecting mirror 17", shown in FIG. I as a concave mirror but which, however, can instead be an angularly disposed planar mirror, if desired.

In place of a grating one can use a prism, if desired. The grating 14 can be either a reflection, diffraction or transmission grating. The grating 14 splits the light from the light source 12 into various wavelengths. The split light then encounters a means 16 programmed to select the wavelength(s) of choice. The wavelength selecting means 16 can be apparatus containing a plurality of devices having no mechanically moving parts. Such devices may include micro shutters, micro mercury switches, or other devices programmed to select the wavelength(s) of choice. The wavelength selecting means 16 can be changed from a closed to an open condition in any desired sequence, thereby allowing one or more wavelengths to pass through at a time. Thus, one or more wavelengths can be displayed without mechanical scanning or adjustment of either the grating (or prism) 14 or of the wavelength selecting means 16.

Among the wavelength selecting means 16 particularly useful in a random access monochromator constructed in accordance with this invention are fast micro mercury switches and fast micro shutter arrays that work on a micro shutter system, operated by electrostatic or electromagnetic forces in the microsecond to millisecond time domain. The fast micro mercury switches and fast micro shutter arrays preferred for use in practicing this invention are ones that do not alter the characteristics of the original light, other than by selecting an individual wavelength or wavelengths and by controlling bandwidth. One commercially available fast micro shutter array suitable for use in the random access monochromators of this invention is the CSEM fast micro shutter system sold by CSEM of Neufchatel, Switzerland.

A micro shutter system, designated generally as 20 in FIG. II, is comprised of a transparent substrate 21, typically formed of quartz, glass, Suprasil or Durasil purified glass, or the like. FIG. II shows transparent substrate 21 cut away y- on the left to expose rows of non-transparent strips 22 which are attached to or deposited onto the transparent substrate 21. The non-transparent strips 22 may be made of material such as metal, e.g., aluminum or alloy steel, or opaque plastic or the like. An electrostatic generating force-controller 23 is attached to the non-transparent strips 22 to control the operating condition of the non-transparent strips 22. A spectrum of wavelengths of light is displayed on the shutter system 20 in such a way that each non-transparent strip has a different wavelength of light from the grating or prism 14 displayed on it. The controller 23 permits the selective opening of one or more of the shutters 20 at will, using electrostatic forces generated by on/off electrical signals from the controller. By opening more than one shutter 20 side by side, one can vary the bandwidth of the wavelength of light from the light source 12. The shutters 20 function totally independently of one another. This means there is no interference between the individual elements to adversely affect the wavelengths. The width of the shutters 20 ultimately governs the resolution of the device. Because the shutters 20 are not mechanically moved, but instead are caused to selectively change their operative condition by electrostatic forces, they respond very quickly, in the microsecond to millisecond time domain. A great plurality of such shutters 20, numbered in hundreds or thousands, can be combined, as desired, allowing for a broad range of wavelength selectivity. The shutters 20 can be stacked horizontally, vertically, or both horizontally and vertically. The substrate 21 upon which the strips 22 are held is transparent to light, and neither affects nor alters the light being transmitted. Appropriate connections 24, schematically represented in FIG. II, between the controller 23 and the strips 22 are provided in an operational random access monochromator of this invention using a micro shutter system, such as the system 20, as the micro shutter wavelength selecting means.

Alternatively, micro mercury switches can be used as the wavelength selecting means 16 in a fashion similar to the above-described micro shutters. A micro mercury switch 30 is shown in FIG. III and is discussed in more detail herein. When micro mercury switches are used, the movement of mercury is used to selectively open and close the switches that, in turn, open and close one or more optical paths, thereby allowing entry of the wavelength(s) of choice. Hence, a plurality of micro mercury switches can be used in place of a plurality of micro shutters. Here too, there are no moving mechanical parts in the random access monochromator, and the speed at which a device of this invention using micro mercury switches can be operated is similar to the speed obtainable using micro shutters. The movement of the mercury in the micro mercury switches can be magnetically controlled by generating a computer programmed alternating magnetic field, using a source of electric current and a permanent magnet or an electromagnet (not shown in FIG. III). The substrate of a preferred micro mercury system is made of a transparent material such as a quartz, glass, purified glass or transparent plastic housing, or the like. The substrate which houses the mercury switches is transparent to light and will neither affect nor alter the transmitted light.

A fast micro mercury switch system, designated generally as 30 in FIG. III, is comprised of a pair of oppositely spaced housings 31, each containing a number of magnetic controllers (not shown). The system further comprises a masked substrate 33 that holds a number of micro mercury switches 32. The arrangement is such that each individual switch 32 is provided with an associated controller in each housing 31. Appropriate connections (not shown) to the respective magnetic controllers permit the selective determination of the operating condition of the respective switches whereby wavelength selection can be effected.

Reference is now made to FIG. I. After leaving the wavelength selection means, the desired wavelengths may encounter an optical element 19 such as a mirror which directs the desired wavelengths to deflecting mirror 17". After processing in the manner described, light of the desired wavelength(s) is passed through a slit 18 in the wall 11" of the apparatus, or directly from the wavelength selecting means 16, to a detector surface not shown, such as a photo diode array. Various optical elements constituting a recombination optics system, e.g., the optical elements shown in FIG. I as 17, 17', 17" and 19, can also be used, if desired, to orient the light in various directions. Numerous variations or combinations of such optical elements, if used, are available, and their positioning is not material to the invention. The combination of two gratings or prisms, the second of them being positioned in place of the optical element 19, can also be used when practicing this invention.

The foregoing discussion of this invention is directed primarily to preferred embodiments thereof. Further modifications are also possible, without departing from the inventive concept, that will furnish random access monochromators which are capable of rapid movement and which contain high speed means for randomly selecting at least one wavelength of light split from an original light source whose individual elements are controllable on an individual basis. Such monochromators will also contain no medium that will alter the characteristics of the original light source, e.g., cause polarization or light losses beyond the usual transmission loss, when said high speed means is open. Accordingly, it will be readily apparent to those skilled in the art that still further changes and modifications in the actual implementation of the concepts described herein can readily be made without departing from the spirit and scope of the invention as defined by the following claims.

We claim:

1. A random access monochromator, comprising:
   means for splitting light into various wavelengths;
   a micro shutter system for randomly selecting at least one wavelength of the thus-split light,
   means for directing the selected wavelength(s) to another area of the monochromator; and
   means for passing the selected wavelength(s) to a location outside the monochromator.

2. The monochromator of claim 1, the micro shutter system further comprising:
   a transparent substrate;
   a plurality of non-transparent strips attached to or deposited onto the transparent substrate; and
   an electrostatic force-controller operatively coupled to the non-transparent strips.

3. The monochromator of claim 1, the micro shutter system further comprising a plurality of individual elements which function independently of one another.

4. The monochromator of claim 1, the micro shutter system being capable of selecting more than one wavelength of the thus-split light.

5. The monochromator of claim 4, the micro shutter system being further capable of selecting more than one wavelength of the thus-split light simultaneously.

6. The monochromator of claim 4, the micro shutter system being further capable of selecting more than one wavelength and varying spectral band width simultaneously.

7. The monochromator of claim 1, the micro shutter system being capable of varying the spectral band width of the selected wavelength.

8. A random access monochromator, comprising:
   means for splitting light into various wavelengths;
   a micro mercury switch system for randomly selecting at least one wavelength of the thus-split light;
   means for directing the selected wavelength(s) to another area of the monochromator; and
   means for passing the selected wavelength(s) to a location outside the monochromator.

9. The monochromator of claim 8, the micro mercury switch system further comprising:
   a transparent substrate;
   a plurality of micro mercury switches attached to the substrate; and
   first and second housings oppositely spaced in proximity to the substrate, the first and second housings including a plurality of magnetic controllers operatively coupled to the micro mercury switches.

10. The monochromator of claim 8, the micro mercury switch system further comprising a plurality of individual elements which function independently of one another.

11. The monochromator of claim 8, the micro mercury switch shutter system being capable of selecting more than one wavelength of the thus-split light.

12. The monochromator of claim 11, the micro mercury switch system being further capable of selecting more than one wavelength of the thus-split light simultaneously.

13. The monochromator of claim 11, the micro mercury switch system being further capable of selecting more than one wavelength and varying spectral band width simultaneously.

14. The monochromator of claim 8, the micro mercury switch shutter system being capable of varying the spectral band width of the selected wavelength.

* * * * *